United States Patent [19]

Rose et al.

[11] Patent Number: 5,015,950
[45] Date of Patent: May 14, 1991

[54] METHOD AND APPARATUS FOR DETERMINING THERMAL RESISTANCE AND STRUCTURAL INTEGRITY OF COATINGS ON CONDUCTING MATERIALS BY MONITORING ELECTRICAL CONDUCTANCE OF THE UNDERLYING MATERIAL UPON LOCALIZED HEATING OF THE OVERLYING COATING

[75] Inventors: James H. Rose; John C. Moulder, both of Ames, Iowa

[73] Assignee: Iowa Sate University Research Foundation, Inc., Ames, Iowa

[21] Appl. No.: 383,799

[22] Filed: Jul. 21, 1989

[51] Int. Cl.[5] .................. G01N 27/72; G01R 33/00; G01R 31/00
[52] U.S. Cl. ................................ 324/224; 324/501
[58] Field of Search ............... 324/224, 501, 158 R, 324/158 D; 374/4, 5, 45, 57

[56] References Cited

U.S. PATENT DOCUMENTS

| | | |
|---|---|---|
| 2,386,319 | 10/1945 | Johnson . |
| 2,852,850 | 9/1958 | Martin . |
| 2,920,268 | 1/1960 | Young .................................. 324/230 |
| 3,626,344 | 12/1971 | Shakernikov et al. . |
| 3,986,105 | 10/1976 | Nix et al. . |
| 4,522,510 | 6/1985 | Rosencwaig et al. . |
| 4,632,561 | 12/1986 | Rosencwaig et al. . |
| 4,634,291 | 1/1987 | Bantel et al. . |
| 4,673,877 | 7/1987 | Sakamoto et al. . |
| 4,679,946 | 7/1987 | Rosencwaig et al. . |
| 4,695,797 | 9/1987 | Deutsch et al. . |
| 4,739,258 | 4/1988 | Schwarz .............................. 324/702 |

Primary Examiner—Walter E. Snow
Attorney, Agent, or Firm—Zarley, McKee, Thomte, Voorhees & Sease

[57] ABSTRACT

A system for nondestructive analysis of barrier coatings on electrically conductive materials includes imposition of a controlled known heat load to a localized area of the coating and measuring electrical conductivity of the underlying material at or near the localized area of the coating. The electrical conductivity of the material is affected by changes in temperature related to thermal conduction into the material through the coating. Thermal resistance of the coating and defects between the coating and the material can therefore be detected.

19 Claims, 1 Drawing Sheet

METHOD AND APPARATUS FOR DETERMINING THERMAL RESISTANCE AND STRUCTURAL INTEGRITY OF COATINGS ON CONDUCTING MATERIALS BY MONITORING ELECTRICAL CONDUCTANCE OF THE UNDERLYING MATERIAL UPON LOCALIZED HEATING OF THE OVERLYING COATING

BACKGROUND OF THE INVENTION

1. Field of the Invention

The present invention relates to analyzing coatings on electrically conducting materials, and in particular, analyzing non-conducting coatings on electrically conducting substrates.

2. Problems in the Art

Many metal parts utilized in critical situations have coatings which attempt to protect those part from high temperature, chemicals, wear, or other dangers. An example is coatings on the metal parts of jet aircraft engines; these coatings are called thermal barrier coatings (TBC) and play a critical role in current airplane technology.

Coatings are also utilized to provide barriers to chemical attack, to improve wear, and to provide other desirable mechanical properties.

As can be appreciated, many coatings are relatively thin and therefore, to be effective, it is essential that their thickness and integrity be as uniform and complete as possible. For example, thermal barrier coatings are typically 100 to 500 micrometer thick layers of ceramic materials such as yttria-stabilized zirconia bonded to a metallic component. Obviously, thermal barrier coatings have low thermal conductivity which limits the heat load to the metal part in a high temperature environment.

Many coatings of these types are bonded directly to the metal substrate. Once bonded, there is no easy way to evaluate the coating for thickness and integrity.

Attempts have been made to nondestructively evaluate coatings, but to present, these attempts have not adequately been able to characterize relevant defects such as inadequate thickness, porosity, disbonds or cracks at the coating/substrate interface, or other flaws. A real need therefore exists for a nondestructive evaluation (NDE) technique which can measure the protection offered by the coating, for example, its thermal resistance, and/or determine the coating's structural integrity.

It is therefore a principal object of the present invention to provide a means and method for nondestructively analyzing coatings on electrically conducting materials which solves or improves over the problems and deficiencies in the art.

A further object is to present a means and method as above described which is nondestructive and accurate in measuring characteristics such as inadequate thickness, porosity, disbonds, cracks, or flaws in the coating.

Another object of the present invention is to provide a means and method as above described which is efficient, economical, and reliable.

A further object of the present invention is to provide a means and method as above described which is flexible with regard to its application to a variety of coatings and electrically conducting materials and in its ability to characterize defects in coatings.

These and other objects, features, and advantages of the present invention will become more apparent with reference to the accompanying specification and claims.

SUMMARY OF THE INVENTION

The present invention is a means and method for nondestructively analyzing non-conductive coatings on electrically conducting materials. A heat load is imposed upon the coating in a controlled fashion. The electrical conductivity of the electrically conducting substrate material is then monitored. The characteristics and nature of the coating at the point of electrical conductivity measurement can then be derived by monitoring the changes in conductivity of this substrate material at that point.

Increased temperature to a metallic or conducting substrate causes change in its conductivity. The effectiveness of the coating, such as thickness, can therefore be analyzed by controlling the heat load and monitoring the electrical conductivity of the electrically conducting substrate at that point.

Thickness of the coating, disbonds, flaws, or cracks, or other defects can be detected. Therefore, thermal resistance of the coating can be measured for thermal barrier coatings, or the structural integrity of the coating, for any type of coating, can be analyzed.

DETAILED DESCRIPTION OF THE PREFERRED EMBODIMENT

Figure 1:
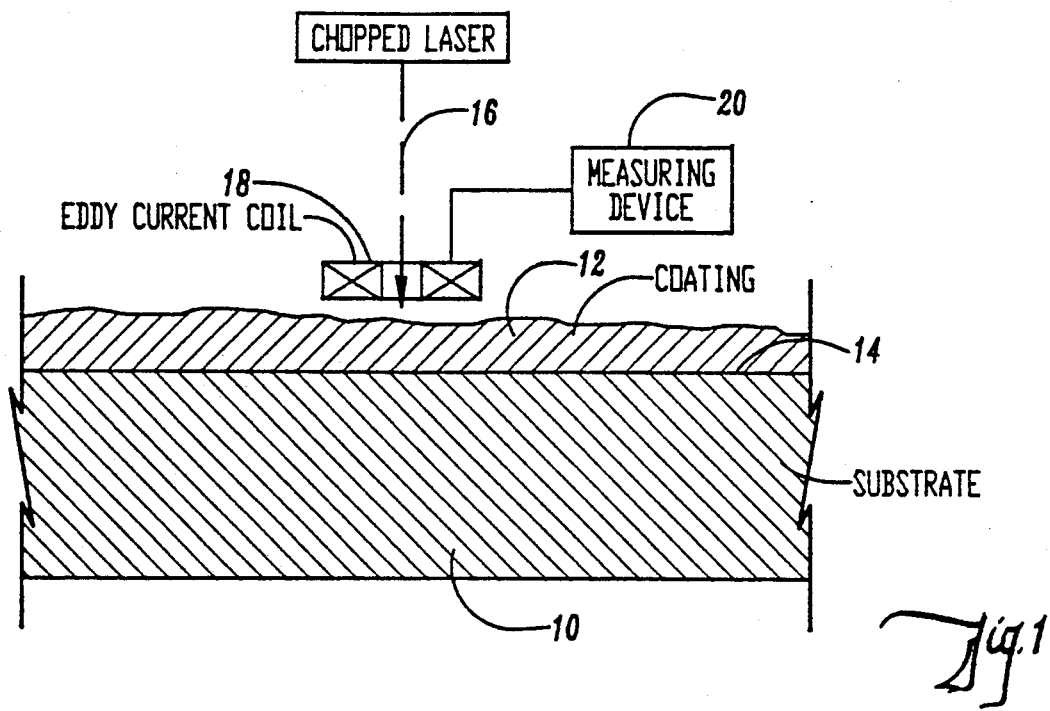
FIG. 1 is a schematic elevational sectional view of one embodiment of the present invention.

By referring to the drawings, a detailed description of the preferred embodiments of the present invention will be described. This description is intended to aid in an understanding of the invention, but is not meant to limit the invention. Reference numerals will be utilized to identify parts in the drawings.

In FIG. 1, there is shown a first embodiment of the present invention. An electrically conducting part or substrate 10 has a barrier coating 12 bonded to its surface 14. A chopped laser beam 16 is imposed upon coating 12 at a localized area of coating 12. An eddy current coil 18, such as well known in the art, is positioned adjacent the upper surface of coating 12 so that the beam 16 is coaxial with coil 18.

Coil 18 is connected to a measuring device 20 such as is commonly used to accept and record the signals from coil 18.

In operation, the configuration of FIG. 1 works as follows:

Beam 16 is chopped so as to allow variable modulation of the beam upon the surface of coating 12. Beam 16 is also focused creating a small localized hot spot on coating 12. Thermal waves (critically damped, diffusive heat waves with a characteristic thermal diffusion length that depends on the modulation frequency) carry the heat into substrate 10 causing a temperature-induced change in the electrical conductivity of substrate 10.

Eddy current coil 18 detects this change in conductivity. The eddy current coil of probe 18 is simple, efficient, and nondestructive in that it can be non-contacting to the barrier coating 12.

Eddy current coil 18 operates by measuring changes in the AC impedence of its coil when the coil is brought into the vicinity of substrate 10. Changes in substrate 10's electrical conductivity effect the impedance of coil 18.

To measure thermal resistance of coating 12, the laser beam 16 could be modulated, and coil 18 moved relative to the upper surface of coating 12. Measuring device 20 would then record the thermally induced changes in the eddy current coil 18's impedance. These changes would be proportional to the total change in substrate 10's conductivity, which in turn depends on the total heat transported across coating 12. Thermal resistance would then be a function of the position of coil 18. It is also possible by monitoring coil 18's impedance (without respect to temperature changes) to measure the thickness of coating 12.

Defects in coating 12 could also be detected as they generally strongly affect the temperature, and therefore the electrical conductivity, of the substrate 10 in their immediate vicinity. By controlling the heating pattern of laser beam 16 through periodic or transient heating controlled by modulation (time varying) operation of beam 16, disbonds, cracks, and other flaws between the coating and substrate 10 can be discerned. Alternatively, heating could be controlled by a programmable heating source if desired.

Beam 16 could be operated to periodically heat small localized areas of coating 12. The period or modulation of beam 16 would be controlled first to be of high frequency. Thermal diffusion length would therefore be small and little heat energy would penetrate through coating 12 to substrate 10. Monitoring of conductivity by coil 18 would therefore remain fairly constant.

By reducing modulation frequency (i.e., the frequency of the periodic heating), thermal diffusion length increases. Heat energy would penetrate further and further into substrate 10 with continued reduction of modulation frequency. If the coating 12 does not have any flaws or defects at that location, the signal from coil 18 due to temperature-induced change in electrical conductivity would increase sharply over the sweep from high to low modulation frequencies.

However, if a disbond exists between coating 12 and substrate 10 at that point, in the sweep from high to low frequency, the gap would tend to allow little, if any, heat to penetrate to substrate 10. As a result, the signal will be very small and independent of modulation frequency. In other words, by monitoring measuring device 20, it would be seen that the signal was not increasing as it should be thereby indicating some sort of a gap or disbond between a coating 12 and substrate 10 at that point.

It can therefore be seen that the frequency dependence of the signal, as well as its overall magnitude, allow discrimination between good regions of coating 12 and disbonds.

In the preferred embodiment of FIG. 1, the laser beam is modulated by chopping it such as is well known in the art. It is to be understood that chopping has the further advantage in subsequent signal processing to allow use of lock-in amplifiers to improve the signal to noise ratio of the device, if utilized.

It can further be understood that by sweeping modulation frequency from high to low, the onset of the signal would serve as an independent gauge of the thickness of coating 12. By utilizing sufficiently focused laser beams, small flaws or disbonds can be detected as well as porosity, voids, inclusions, or cracks which can affect performance of coating 12.

The included preferred embodiment is given by way of example only, and not by way of limitation to the invention, which is solely described by the claims herein. Variations obvious to one skilled in the art will be included within the invention defined by the claims.

Figure 2:
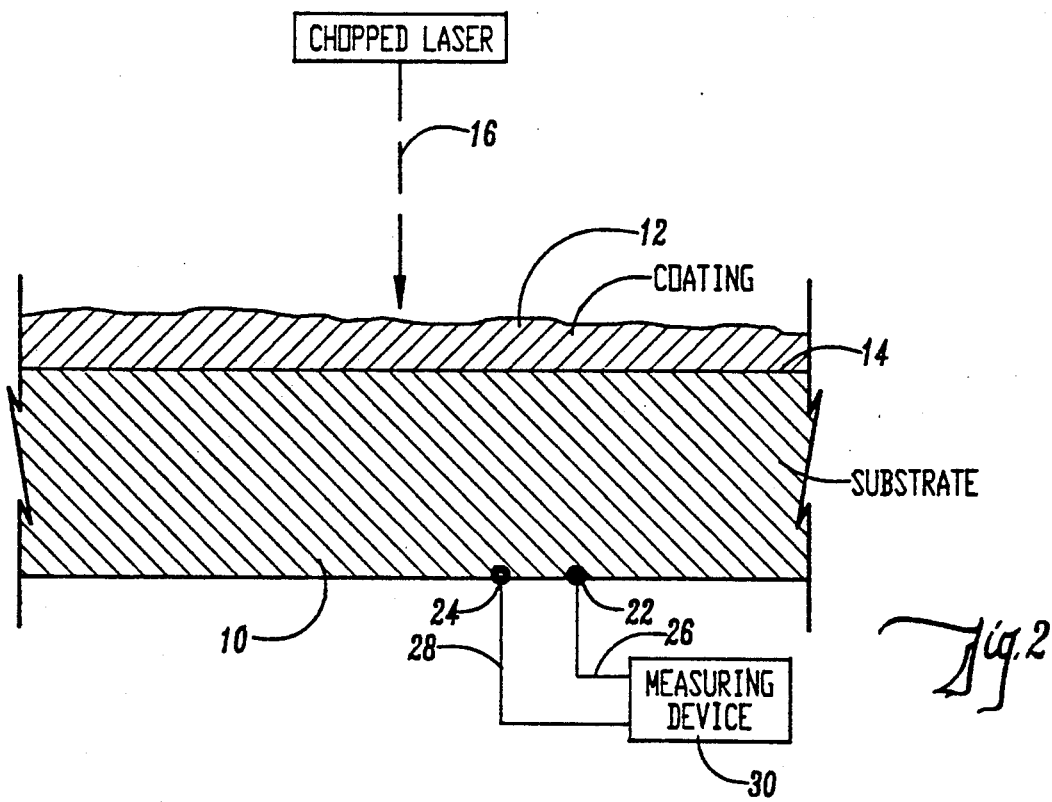
FIG. 2 is a schematic elevational sectional view of a second embodiment of the present invention.

For example, FIG. 2 schematically depicts an alternative device for measuring electrical conductivity of substrate 10. Electrical probes 22 and 24 are connected in electrical communication with substrate 10 at spaced apart positions along a surface of substrate 10. Electrical probes 22 and 24 are communicated by wires 26 and 28 to measuring device 30 which, as is well known in the art, is an electrical conductance measuring device.

By positioning electrical probes 22 and 24 sufficiently close to the location and position of laser beam 16 to substrate 10, the electrical conductance of substrate 10 can be monitored around that location of substrate 10. It is noted that the electrical conductance measuring device could be positioned on the same side as the coating (FIG. 1) or on the opposite side (FIG. 2, for example).

It is to be understood that the present invention is applicable to a wide variety of coatings and electrically conductive substrates, including but not limited to ceramic coatings and metallic substrates.

Furthermore, heating of localized areas of the coating can be accomplished not only by lasers, but also by x-ray or other electromagnetic beams. Furthermore, particle beams could be used such as an electron beam.

Components which could be used with the preferred embodiments of the invention are as follows. The heat source, if a laser, could be an argon-ion laser, Spectra Physics Model 2010, Mountain View, Calif. A HMS light beam chopper, model 222, from Ithaco, Ithaca, N.Y., could be utilized to chop the laser beam to modulate it.

A measuring device could be any sensitive conductivity measurer. An elementary example would be a Hewlett-Packard model 3478A volt meter. If an eddy current probe is utilized, a measuring device would include, in the preferred embodiment, an eddy scope available from Nortec, model NDT-19, Kennewick, Wash. The eddy scope would demodulate the eddy current probe signal which basically presents an analog output signal of the relevant information from the eddy current probe.

A lock-in amplifier would then be connected to the analog output of the eddy scope. The lock-in amplifier would be referenced to the chopping frequency of the chopper and would only amplify portions of the signal at the same frequency. This would eliminate noise components. A lock-in amplifier which could be used is model 5206 from EG&G/Princeton Applied Research, Princeton, N.J.

An eddy current probe or coil could be manufactured or be available from Nortec in Kennewick, Wash.

What is claimed is:

1. A method for nondestructively analyzing coatings on electrically conducting materials comprising: imposing a controlled known heat load to a localized area of the barrier coating; measuring the electrical conductivity of the material at or near
the localized area; and deriving characteristics of the barrier coating at or near the
localized area from the measurement of electrical conductivity.

2. The method of claim 1 further comprising the step of analyzing the measurement of electrical conductivity with regard to thermal resistance of the coating.

3. The method of claim 1 further comprising the step of analyzing the measurement of electrical conductivity with respect to defects in the coating.

4. The method of claim 1 wherein the heat load is generated by imposing an energy source upon the coating.

5. The method of claim 4 wherein the energy source comprises an electromagnetic beam.

6. The method of claim 4 wherein the energy source comprises a particle beam.

7. The method of claim 1 wherein the measurement of electrical conductivity is accomplished by utilizing an eddy current probe.

8. The method of claim 1 further comprising the step of inferring a change in temperature of the material to derive the amount of heat transfer through the coating to the material.

9. A means for nondestructively analyzing coatings on electrical conducting material comprising:
   means for generating and controlling a known heat load directly to a localized area of the coating to raise the temperature of only the localized area in a controlled manner; and
   means to measure electrical conductivity of the material underneath the coating at or near the localized area of the coating to detect whether and to what extent the heat load penetrated the coating and heated the underlying material to in turn discern characteristics of the coating at or near the localized area, including at least thermal resistance, thermal conductivity, thermal diffusivity, thickness, porosity, disbonds, cracks, voids, defects or flaws in the coating.

10. The means of claim 9 wherein the coating is a thermal barrier coating.

11. The means of claim 9 wherein the means for generating a known heat load comprises a beam of electromagnetic radiation.

12. The means of claim 11 wherein the beam of electromagnetic radiation comprises a laser beam.

13. The means of claim 11 including a modulation means for modulating the beam of electromagnetic radiation.

14. The means of claim 9 wherein the means to measure electrical conductivity of the material comprises an eddy scope means for processing the eddy scope signal to an analog output.

15. The means of claim 9 wherein the means to measure electrical conductivity further comprises an eddy current scope including an eddy current coil.

16. The method of claim 1 further comprising the step of analyzing the measurement of electrical conductivity with respect to any of the characteristics including at least thermal resistance, thermal conductivity, thermal diffusivity, thickness, porosity, disbonds, cracks, voids, defects or flaws.

17. A method for nondestructively analyzing coatings on electrically conducting materials comprising:
   imposing a controlled known heat load to a localized area of the barrier coating;
   measuring electrical conductivity of the material at or near the localized area; and
   analyzing the measurement of electrical conductivity with regard to thermal resistance of the coating.

18. A method for nondestructively analyzing coatings on electrically conducting materials comprising:
   imposing a controlled known heat load to a localized area of the barrier coating;
   measuring electrical conductivity of the material at or near the localized area; and
   analyzing the measurement of electrical conductivity with respect to defects in the coating.

19. A method for nondestructively analyzing coatings on electrically conducting materials comprising:
   imposing a controlled known heat load to a localized area of the barrier coating;
   measuring electrical conductivity of the material at or near the localized area; and
   inferring a change in temperature of the material to derive the amount of heat transfer through the coating to the material.

* * * * *